United States Patent
Iger

(10) Patent No.: US 9,883,904 B2
(45) Date of Patent: Feb. 6, 2018

(54) METHOD AND APPARATUS FOR VOLUMETRIC SPECIFIC FRACTIONAL ENERGY IMPACT

(71) Applicant: LUMENIS LTD., Yokneam Ilit (IL)

(72) Inventor: Yoni Iger, Yoqneam (IL)

(73) Assignee: LUMENIS LTD. (IL)

( * ) Notice: Subject to any disclaimer, the term of this patent is extended or adjusted under 35 U.S.C. 154(b) by 621 days.

(21) Appl. No.: 14/366,070

(22) PCT Filed: Dec. 18, 2012

(86) PCT No.: PCT/IB2012/057415
§ 371 (c)(1),
(2) Date: Jun. 17, 2014

(87) PCT Pub. No.: WO2013/093768
PCT Pub. Date: Jun. 27, 2013

(65) Prior Publication Data
US 2015/0073402 A1    Mar. 12, 2015

Related U.S. Application Data

(60) Provisional application No. 61/577,751, filed on Dec. 20, 2011.

(51) Int. Cl.
| A61B 18/14 | (2006.01) |
| A61N 7/00 | (2006.01) |
| A61N 5/06 | (2006.01) |
| A61B 18/00 | (2006.01) |

(52) U.S. Cl.
CPC .......... *A61B 18/14* (2013.01); *A61N 5/0616* (2013.01); *A61N 7/00* (2013.01); *A61B 2018/00291* (2013.01); *A61B 2018/00452* (2013.01); *A61B 2018/1467* (2013.01); *A61N 2007/0078* (2013.01)

(58) Field of Classification Search
CPC .......... A61B 18/14; A61B 2018/00291; A61B 2018/00452; A61B 2018/1467; A61N 2007/0078; A61N 5/0616; A61N 7/00
USPC ...................................... 606/33–50
See application file for complete search history.

(56) References Cited

U.S. PATENT DOCUMENTS

| 2005/0049543 A1 | 5/2005 | Anderson et al. |
| 2005/0251118 A1 | 11/2005 | Anderson et al. |
| 2009/0299361 A1 | 12/2009 | Flyash et al. |
| 2010/0016849 A1 | 1/2010 | Rosenberg |

FOREIGN PATENT DOCUMENTS

| WO | 2010007619 | 1/2010 |
| WO | 2011107885 | 9/2011 |

*Primary Examiner* — Michael Peffley
*Assistant Examiner* — Khadijeh Vahdat
(74) *Attorney, Agent, or Firm* — ISUS Intellectual Property PLLC

(57) ABSTRACT

A method and system for treating a surgical incision to prevent scarring is disclosed. The system comprising an applicator is configured to protrude a target tissue from one or both sides of a surgical incision into a treatment cavity located in the applicator. The system is further configured to deliver fractional treatment, from energy sources located along the inner walls of the treatment cavity, to an incision edge.

9 Claims, 5 Drawing Sheets

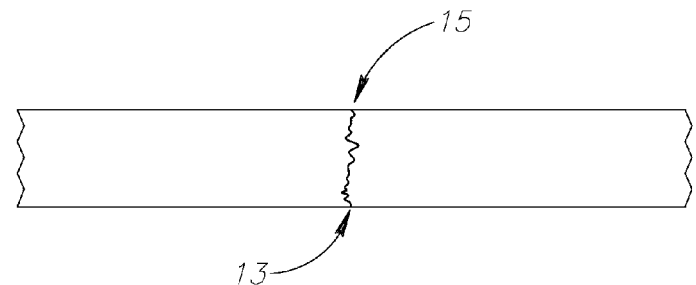

FIG.3

```
┌─────────────────────────────────────────────────────────┐
│  APPLYING A TREATMENT APPLICATOR ON TISSUE              │
│ LOCATED ON ONE OR  BOTH SIDES OF A SURGICAL INCISION    │
└─────────────────────────────────────────────────────────┘
                            │
┌─────────────────────────────────────────────────────────┐
│  PROTRUDING AT LEAST A PORTION OF THE TISSUE, LOCATED   │
│  ON ONE OR BOTH SIDES OF THE SURGICAL INCISION, INTO A  │
│  TREATMENT CAVITY LOCATED IN THE TREATMENT APPLICATOR   │
└─────────────────────────────────────────────────────────┘
                            │
┌─────────────────────────────────────────────────────────┐
│    DELIVERING AN ENERGY ONTO AT LEAST A PORTION OF      │
│   THE TISSUE WITHIN THE TREATMENT CAVITY FROM AT LEAST  │
│   ONE ELECTRODE DISPOSED ALONG THE INTERNAL SURFACE     │
│                 OF THE TREATMENT CAVITY                 │
└─────────────────────────────────────────────────────────┘
                            │
┌─────────────────────────────────────────────────────────┐
│    ACTIVATING THE AT LEAST ONE ELECTRODE TO IRRADIATE   │
│     AT LEAST A PORTION OF THE TISSUE WITHIN THE         │
│                   TREATMENT CAVITY                      │
└─────────────────────────────────────────────────────────┘
```

FIG.4

METHOD AND APPARATUS FOR VOLUMETRIC SPECIFIC FRACTIONAL ENERGY IMPACT

CROSS-REFERENCE TO RELATED APPLICATIONS

The contents of U.S. Provisional Application No. 61/309,352 "METHOD AND APPARATUS FOR VOLUMETRIC SPECIFIC FRACTIONAL ENERGY IMPACT", filed Mar. 1, 2010, and the contents of U.S. patent application Ser. No. 13/038,229, "METHOD AND APPARATUS FOR VOLUMETRIC SPECIFIC FRACTIONAL ENERGY IMPACT", filed Mar. 1, 2011, and the contents of PCT Patent Application No. PCT/IB2011/000715, "METHOD AND APPARATUS FOR VOLUMETRIC SPECIFIC FRACTIONAL ENERGY IMPACT", filed Mar. 1, 2011 are herein incorporated by reference in their entirety.

TECHNICAL FIELD

The present invention relates to a method of fractional tissue treatment and more particularly, to ablative or non-ablative radiofrequency, ultrasound, cryogenic or laser treatment of surgical incisions for scar prevention. The present invention also provides a system for delivering the treatment.

BACKGROUND

Skin integrity loss triggers healing and regeneration processes of the affected tissue. Awry healing processes of the body tissue may result in an exuberance of fibroblastic proliferation and collagen synthesis leading to wound-confined hypertrophic scar formation, while further exuberance can result in keloid scar formation which extends beyond the wound boundaries. These hypertropic, as well as keloidal scars may be itchy or painful in some individuals and may cause aesthetic problem. Surgical incision is one source for skin integrity loss which may trigger such a healing and regeneration process which may then lead to hypertropic or keloidal scar formation. In some cases surgical scars may also lead to atrpoic scarring, resulting from deteriorated impact on fibroblast activity.

BRIEF SUMMARY

One aspect of the invention provides a method for the prevention of scar tissue, the method comprising: applying a treatment applicator on tissue located on one or both sides of a surgical incision; protruding at least a portion of the tissue, located on one or both sides of the surgical incision, into a treatment cavity located in the treatment applicator; wherein the treatment cavity is provided with at least one electrode disposed along the internal surface of the treatment cavity; and activating the at least one electrode to irradiate at least a portion of the tissue within the treatment cavity.

According to another aspect of the invention, there is provided a system for the prevention of scar tissue, the system for fractional treatment of a condition or pathology including a treatment applicator disposed and configured to deliver treatment energy to a target tissue and defining within its interior a treatment cavity to engage the target tissue. The treatment applicator includes multiple electrodes disposed along predetermined internal surfaces that define the treatment cavity. Each electrode is disposed at an angle relative to the treatment cavity and is configured to generate energy. The electrodes include a first set of at least two electrodes disposed along at least two internal surfaces of the treatment cavity. The at least two electrodes are electronically coupled to operate in a modality to deliver energy to the treatment cavity in a specific direction and at a specific angle so that the electrodes selectively target energy to at least one of: a specific layer, a specific depth, and/or a specific location or depth within a specific layer of a first zone within the target tissue. The first set of electrodes targets energy configured in accordance with one or more parameters to treat the first zone of the target tissue.

According to a further aspect of the invention, there is provided a treatment applicator for providing fractional treatment of a condition or pathology of a tissue, the treatment applicator comprising: a treatment cavity defined within an interior of the treatment applicator and configured to engage a three-dimensional volume of target tissue; multiple electrodes disposed along the internal surfaces defining the treatment cavity, each electrode being disposed at an angle relative to the treatment cavity; an energy source operatively coupled to the multiple electrodes.

at least two electrodes disposed along at least two internal surfaces of the treatment cavity and being electronically coupled to operate in a modality to deliver energy to the treatment cavity in a specific direction and at a specific angle so that the paired electrodes selectively target energy to at least one of: a specific layer, a specific depth, and a specific location or depth within a specific layer to produce one or more different treatment effects within the volume of target tissue.

BRIEF DESCRIPTION OF THE DRAWINGS

For a better understanding of the embodiments of the invention and to show how the same may be carried into effect, reference will now be made, purely by way of example, to the accompanying drawings in which like numerals designate corresponding elements or sections throughout.

In the accompanying drawings:

FIGS. 1-3 are high level schematic illustrations of a surgical incision area;

FIG. 4 illustrates a high level flowchart according to some embodiments of the invention;

Figure 1:
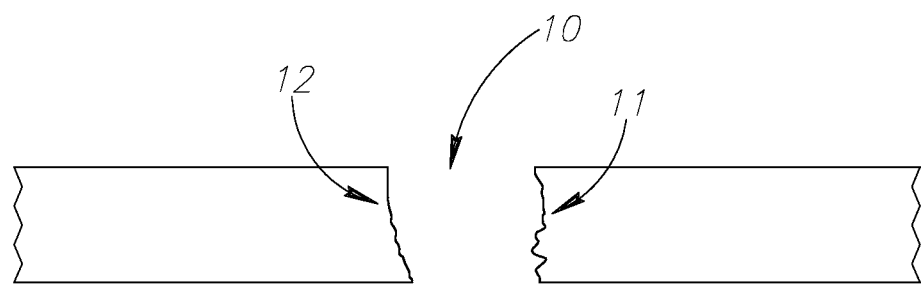

The drawings together with the following detailed description make apparent to those skilled in the art how the invention may be embodied in practice.

DETAILED DESCRIPTION

Prior to setting forth the detailed description, it may be helpful to set forth definitions of certain terms that will be used hereinafter.

The term "electrode" as used herein in this application refers to any type of energy transmitting element or energy irradiating element or energy delivering element. These elements, for example, can be among other things: radiofrequency electrodes, bipolar radio frequency electrodes, light emitting diodes, laser diodes, optical fibers, ultrasound transducers, micro-needle electrodes, cryogenic element etc.

The term "fractional treatment" as used herein in this application refers to a treatment of a target tissue or organ in which at least one treatment point is created in the tissue and is surrounded by non-treated tissue. On a target tissue, one or more treatment points may be created in a variety of sizes, depths, patterns and densities. Fractional treatment may be invasive, non-invasive or any combination of the two.

The term "energy source" as used herein in this application refers to any energy source which may create fractional treatment. As non limiting examples for such energy sources are lasers, non-coherent light sources, radio frequency generators, microwave generators, cryogenically cooled materials, ultrasound etc.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 2:
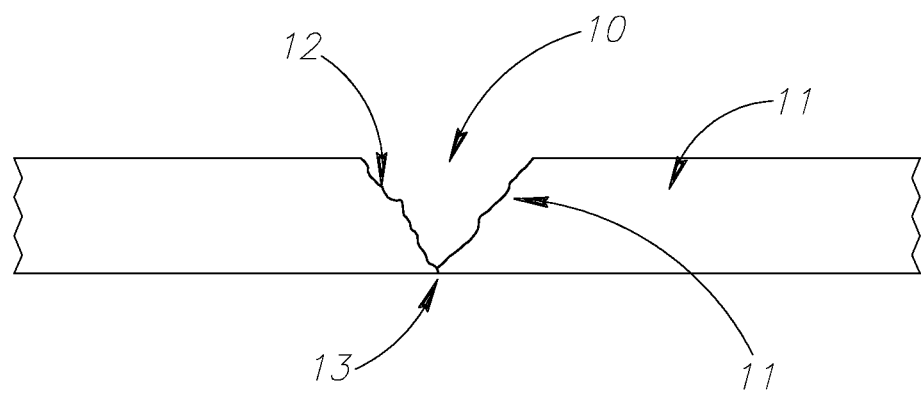

FIG. 1 illustrates a surgical incision 10, a first incision edge 11 and a second incision edge 12, as know in the prior art. FIGS. 2 and 3 illustrate one possible treatment known in the prior art for stitching the incision in two stages. During the first stage, lower and internal layer 13 of the incision 10 is stitched. During the second stage, the external layer 15 of incision 10 is stitched to close the incision. In some cases stage one can be skipped or other methods for closing the incision can be used. As will be discussed below, embodiments of the present invention may be applied to treat a surgical incision even during the current known practice.

FIG. 4 illustrates a high level flow chart according to some embodiments of the invention. In one embodiment of the present invention the method of treatment may include applying a treatment applicator on the tissue located on both sides of a surgical incision. The applicator may be applied so that the incision is aligned with at least one symmetrical axis of the applicator. The applicator may have a length dimension and a width dimension where the length dimension is bigger than the width dimension. In one embodiment, the applicator may be applied in a way that the main long axis of the incision is approximately aligned with the length dimension of the applicator. In yet another embodiment, the width dimension of the applicator may be bigger than its length dimension.

According to one embodiment of the invention, once the applicator is applied on the target tissue on both sides of the incision, a protruding mechanism protrudes at least portions of the target tissue from one or both sides of the incision into a treatment cavity located within the applicator. In at least one embodiment, at least one objective of the applicator is to protrude tissue from one or both sides of the incision along at least a portion of the incision. According to one embodiment of the invention, the applicator is shorter than the incision and multiple treatments may be required in order to cover the full length of an incision. In yet another embodiment of the present invention, the applicator may be the same length as the incision and may capture the entire incision during a single treatment.

In one step according to another embodiment of the present invention, at least a portion of the protruded tissue within the treatment cavity is in contact with at least one electrode which can be activated to irradiate the tissue and to create a fractional treatment. In another embodiment of the present invention, there is no direct contact between the energy source and the target tissue, in this case, the energy travels through free-space to impinge the tissue. This is the case where the energy source is, for example, a laser scanner, a lamp, an infra-red source etc. In another embodiment of the present invention, the energy source may be remote from the target tissue. In this case, an energy delivery system, for example, optical fibers, waveguides etc may be used to deliver the energy to the target tissue. The energy delivery system may be in direct contact with the target tissue or the energy is delivered through free-space. In yet another embodiment of the present invention, multiple electrodes may be activated simultaneously or in a predefined pattern to create a fractional treatment effect on or adjacent incision edges.

Figure 5:
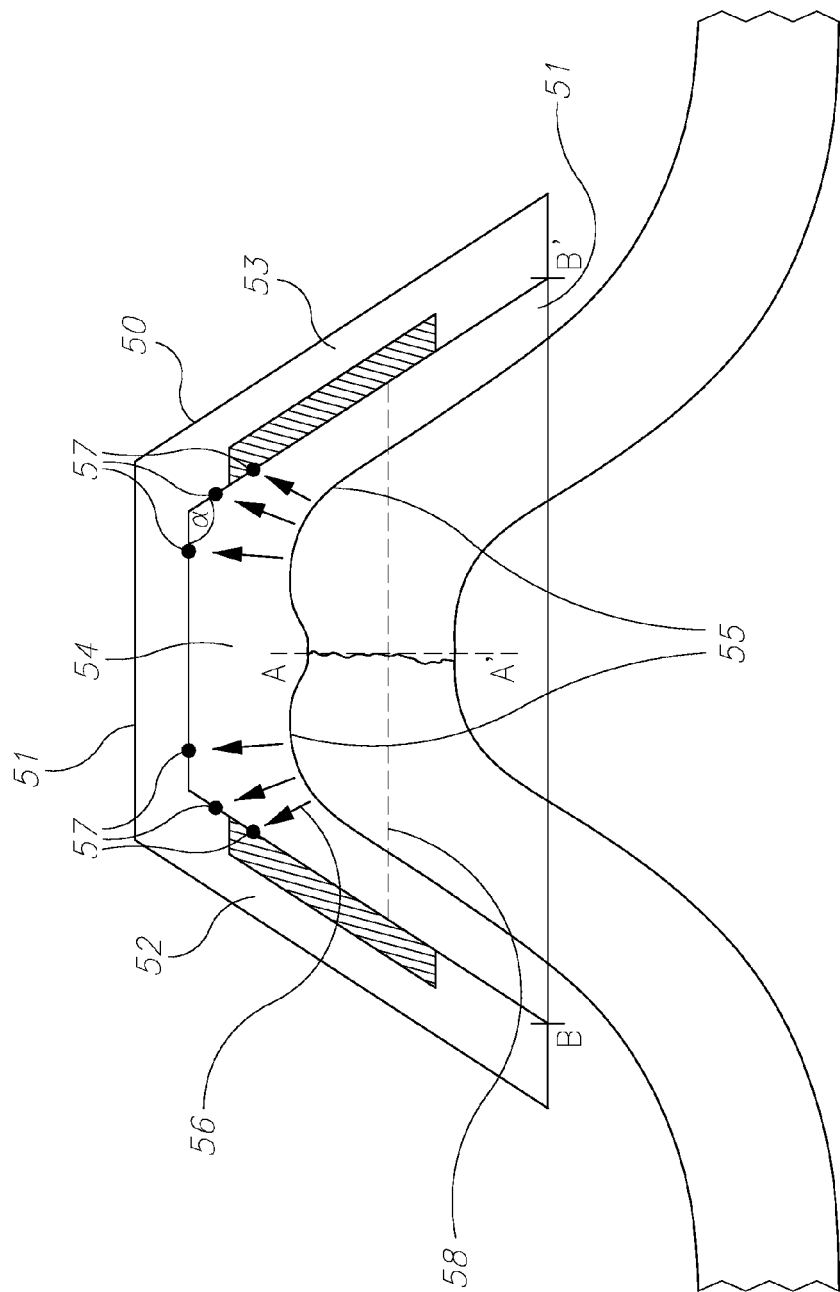
FIG. 5 illustrates one conceptual configuration of the treatment applicator.

FIG. 5 illustrates one configuration of the applicator according to one embodiment of the present invention. Applicator 50 has a base 51 and extending walls 52 and 53. Walls 52 and 53 define a treatment cavity 54 having an aperture 51 with a size BB'. According to one embodiment of the present invention, walls 52 and 53 can rotate and change angle alpha with cavity base 51 so that the aperture size BB' can be changed. In yet another embodiment, the aperture BB' may be changed by sliding walls 52 and 53 relative to base 51. An adjustable aperture size may create a protruding mechanism to protrude the target tissue from both sides of the incision up into the treatment cavity to locate the incision between the electrodes. In yet another embodiment of the present invention the protruding mechanism may be a vacuum based mechanism. According to one embodiment, at least one vacuum channel 57 is located within the treatment cavity and is in fluid communication with a vacuum source. In another embodiment of the present invention multiple vacuum ports may be used. The vacuum ports may be located along base 51 and walls 52 and 53. In order not to create too strong shear forces which are coplanar with the cross section of the incision, on the incision which may open the incision, the vacuum ports may be located off-centered so that no ports protrude the incision itself and its adjacent area. In yet another embodiment, the off-centered vacuum ports may create two shoulders 55 by applying off-centered vacuum force vectors 56.

Vacuum ports 57, according to one embodiment of the present invention, may help to protrude the target tissue into the treatment cavity and to create the contact between the target tissue and electrodes. Vacuum ports 57, in another embodiment, may help to position the target tissue within the treatment cavity in such a way that treatment energy vectors 58 cross incision plane AA'.

Figure 6:
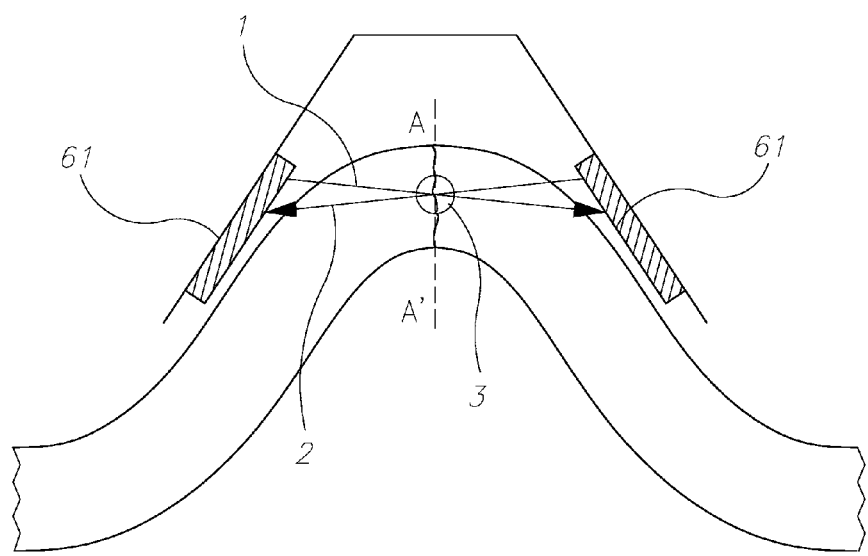
FIG. 6 schematically illustrates another configuration of the treatment applicator.

FIG. 6 illustrates another embodiment of the present invention. According to this embodiment, multiple electrodes elements 61 located on the internal surfaces of treatment cavity are configured to irradiate the target tissue with multiple treatment energy vectors 58. In one embodiment, treatment energy vectors 58 may cross each other adjacent to the incision plane AA'. According to this embodiment, a higher energy fluence may be delivered to an area adjacent to the incision edges 3 to increase the fractional treatment effect while lower energy fluence is delivered to tissue not adjacent to incision plane AA' where treatment in not required.

Figure 7:
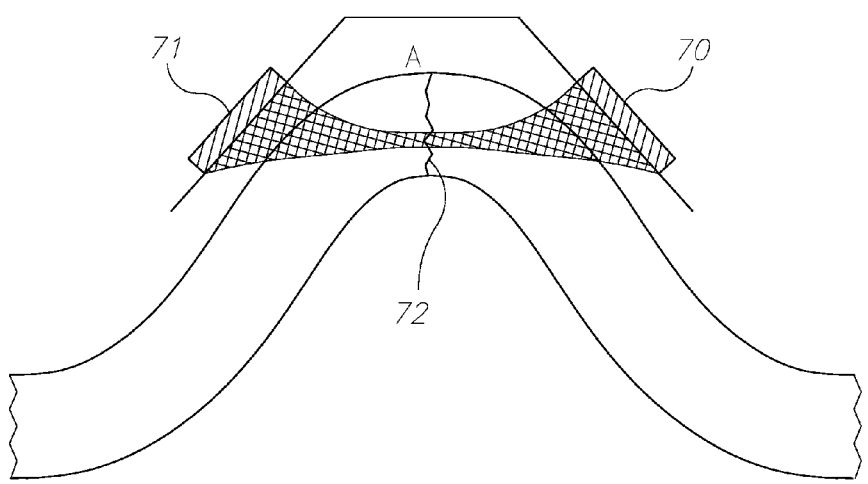
FIG. 7 illustrates another conceptual configuration of the treatment applicator.

FIG. 7 illustrates another embodiment of the present invention where multiple electrodes may be focused to smaller spot sizes in an area adjacent to the incision plane AA' to increase fractional treatment effect on the area of the incision while keeping other tissue areas, where no treatment effect is required, with lower energy fluences. In another embodiment, multiple, separate, treatment energy vectors 58, may be focused to increase its own energy fluence at an area approximately adjacent to the incision edges. In yet another embodiment, a phase array of electrodes may be operated to shift the mutual focal point approximately along at least a portion of the incision edges. According to another configuration, the phase array may be operated in a pulse mode to create discrete fractional treatment points adjacent incision plane AA'.

Figure 8:
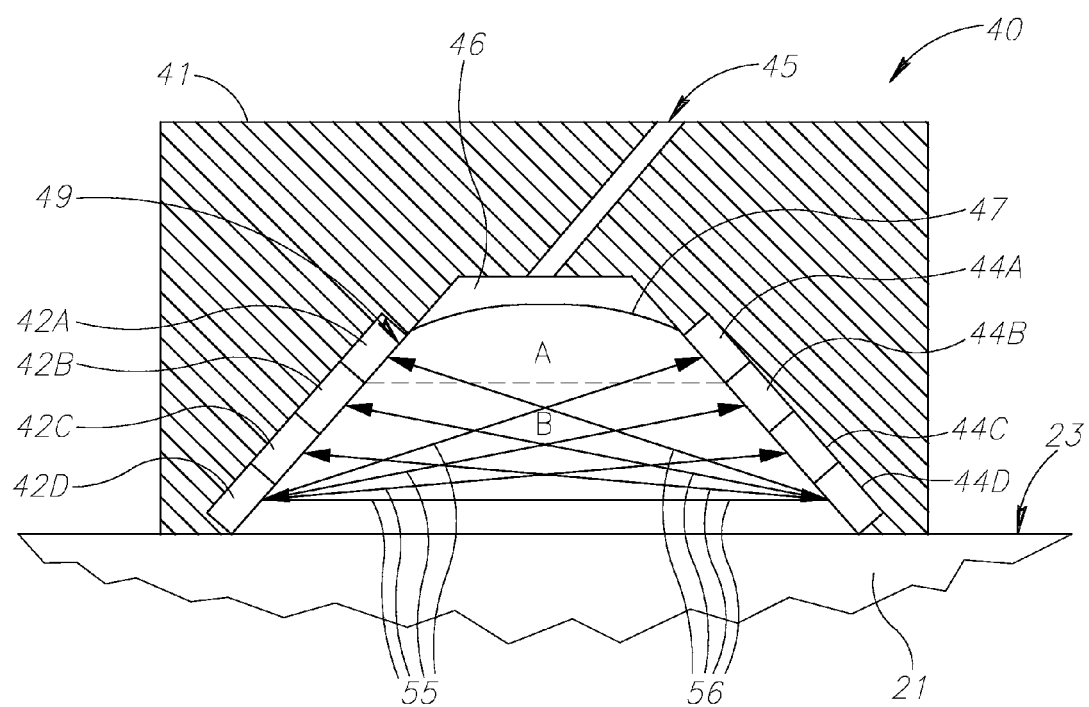
FIG. 8 illustrates another embodiment of a system for the fractional treatment for scar prevention.

Referring to FIG. 8, another illustrative arrangement and configuration of an electronically coupled multiple electrodes 42A-44D and 44A-44D RF is shown. The electrodes may be, for example, bipolar radio frequency electrodes, cryogenic element or ultrasound transducers. The electrodes 42A-44D and 44A-44D shown in FIG. 8 may be programmed and/or operated in accordance with parameters set by a system, and/or the treatment applicator 40, to activate independently, simultaneously, sequentially and/or in a given order or pattern relative to operation of one or more of the other electrodes. In addition, one or more electrodes 42A-42D may be programmed and/or operated to conduct current with one or more other electrodes 44A-44D with which they are electronically coupled to target energy in one or more different directions and at one or more different angles.

For instance, one electrode 42D may be programmed and/or operated to activate alone or in conjunction with the other electrodes 42A-42C and to conduct current with each electrode 44A-44D with which it is electronically coupled to target energy in specific and different directions and at specific and different angles, as illustrated by arrows 55 shown in FIG. 8. In this configuration, the electrode 42D may be programmed and/or operated to activate to conduct current with each electrode 44A-44D in a sequential pattern, or to conduct current simultaneously with each electrode 44A-44D. Energy is thereby delivered in multiple and different directions and angles. As a result of the different directions and different angles with which the electrode 42D conducts current with the electrodes 44A-44D, energy may flow through different tissue layers and/or different depths of the target tissue 47 positioned within Zone A and within Zone B or to the incision edges before closing the incision. Of course, where ultrasound transducers are used, ultrasound energy will flow through different tissue layers. Electrode 42D can thereby target fractional energy to Zone A and Zone B to provide fractional treatment, along X, Z, and/or Y axes, of the volume of target tissue 47 or the edges of the incision, that produces tissue layer specific and/or tissue depth specific treatment effects. Where a laser is used, laser energy delivers fractional energy to the target tissue.

Still referring to FIG. 8, in another instance, any of the electrodes 42A, 42B, 42C and 42D may be programmed and/or operated to activate to conduct current with the electrode 44D with which they are electronically coupled to target energy in specific and different directions and at specific and different angles, as illustrated by arrows 56 shown in FIG. 8. Each electrode 42 A, 42B, 42C and 42D may conduct current with electrode 44D sequentially and/or simultaneously. As a result of the different directions and different angles with which the electrodes 42A-42D conduct current with the electrode 44D, energy may flow through different tissue layers and/or different depths of the target tissue 47 positioned within Zone A and within Zone B or to the edges of the incision. Electrodes 42A-42D can thereby target fractional energy to Zone A and Zone B, or to the edges of the incision before closing the incision, to provide fractional treatment, along X, Z, and/or Y axes, of the volume of target tissue 47 that produces tissue layer specific and/or tissue depth specific treatment effects.

Similarly, one or more of the fractional electrodes 42A1-A8, B1-B8, C1-C8, D1-D8 and 44 B1-B8, C1-C8 D1-D8, and/or one or more individual fractional electrodes, may be programmed and/or operated to activate at the same or different times relative to the other fractional electrodes and/or other individual fractional electrodes to conduct current between electronically coupled electrodes and fractional electrodes as described above. Fractional electrodes, and/or individual fractional electrodes, may activate independently, simultaneously, sequentially and in any order or pattern relative to other electrodes and individual fractional electrodes to deliver energy in different directions and at different angles to the volume of target tissue 47, such that, the energy produces tissue layer specific and/or tissue depth specific treatment effects within Zone A and within Zone B or to the edges of the incision before the incision is closed.

In addition, the multiple electrodes 42A-42D and 44A-44D, or fractional electrodes 42A1-A8, B1-B8, C1-C8, D1-D8 and 44 B1-B8, C1-C8, D1-D8 and/or one or more individual fractional electrodes, may activate, or may be operated by a system and/or the treatment applicator 40, in a continuous mode to deliver continuous currents for a specific length of time, or, alternatively or additionally, may operate in a pulsed mode to deliver pulsed current with specific pulse duration, width, and frequency. These parameters would depend on the tissue treatment application and the heating profiles required or desired within the target tissue to produce customized tissue-specific and depth-specific treatment impacts.

Further, one or more of the electrodes 42A-42D and 44A-44D, illustrated in FIG. 8 may include one or more micro-needle electrodes designed and constructed to precisely target and deliver energy directly into the volume of target tissue 47 and, more particularly, into a specific layer and/or depth of the target tissue 47 or to the edges of the incision tissue before the incision is closed. The micro-needles may be, for example, bipolar RF micro-needle electrodes which are designed for minimally invasive tissue treatment and are configured to confine a heating profile within the target tissue 47 between the bipolar needle pairs. Alternatively, one or more of the electrodes 42A-42D and 44A-44D may include an array of micro-needle electrodes. Like the electrodes 42A-42D and 44A-44D, the arrays of micro-needle electrodes may be selectively electronically coupled and programmed and/or operated to activate to conduct current as described above to target energy to specific tissue types, layers, and/or depths to thereby achieve multiple and different treatment effects, e.g., within Zone A and within Zone B or to the edges of the incision before the incision is closed.

In the above description, an embodiment is an example or implementation of the invention. The various appearances of "one embodiment", "an embodiment" or "some embodiments" or "embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Furthermore, it is to be understood that the invention can be carried out or practiced in various ways and that the invention can be implemented in embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention.

What is claimed is:

1. A cosmetic method of treating a surgical incision in skin tissue to prevent scarring, comprising:
    applying a treatment applicator over the surgical incision in the skin tissue;
    protruding at least a portion of the skin tissue on both sides of the surgical incision into a treatment cavity located in the treatment applicator; wherein the treatment cavity includes multiple electrodes disposed along each of two or more internal surfaces of the treatment cavity,
    activating the multiple electrodes and fractionally irradiating at least a portion of the skin tissue within the treatment cavity;
    wherein the fractional irradiating comprises irradiating with treatment energy vectors in directions across the surgical incision within the treatment cavity;
    wherein the irradiating with the multiple electrodes disposed along each of the two or more internal surfaces of the treatment cavity further comprises delivering energy into the treatment cavity to multiple zones in the skin tissue positioned within the treatment cavity, the energy delivered being different in each of the multiple zones.

2. The method according to claim 1, wherein the step of irradiation of the skin tissue within the treatment cavity further comprises irradiating with one or more of radiofrequency energy or ultrasound energy.

3. The method according to claim 1, wherein the protruding of the at least a portion of the skin tissue located on both sides of the surgical incision further comprises applying negative pressure within the treatment cavity to pull into and retain the skin tissue protruded within the treatment cavity.

4. The method according to claim 3, wherein the application of the negative pressure further comprises applying off-centered vacuum force vectors, and wherein the applying of off-centered vacuum force vector further comprises reducing the shear stress which is approximately coplanar with the cross section of the incision within the treatment cavity.

5. The method according to claim 1, wherein the protruding of the at least a portion of the tissue located on one or both sides of the surgical incision, further comprises changing the aperture size of the treatment cavity.

6. The method according to claim 5, wherein the changing of the aperture size of the treatment cavity further comprises changing the angle between the treatment cavity base and the treatment cavity walls extending from the base.

7. The method according to claim 1, wherein the fractional irradiating treatment of the at least a portion of the skin tissue within the treatment cavity further comprises creating fractional treatment to at least a portion of one edge of the surgical incision.

8. The method according to claim 1, wherein the irradiating with multiple electrodes disposed along each of the two or more internal surfaces of the treatment cavity further comprises crossing multiple treatment energy vectors across the surgical incision within the treatment cavity.

9. The method according to claim 1, wherein the irradiating with multiple electrodes disposed along each of the two or more internal surfaces of the treatment cavity further comprises focusing multiple treatment energy vectors across the surgical incision within the treatment cavity.

* * * * *